United States Patent
Jeong et al.

(10) Patent No.: US 10,143,432 B2
(45) Date of Patent: Dec. 4, 2018

(54) X-RAY APPARATUS AND CONTROL METHOD FOR THE SAME

(71) Applicant: SAMSUNG ELECTRONICS CO., LTD., Suwon-si (KR)

(72) Inventors: Kye Yong Jeong, Suwon-si (KR); Young Hun Sung, Hwaseong-si (KR); Dong-Goo Kang, Hwaseong-si (KR); Ji Young Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 355 days.

(21) Appl. No.: 15/017,892

(22) Filed: Feb. 8, 2016

(65) Prior Publication Data
US 2016/0350910 A1    Dec. 1, 2016

(30) Foreign Application Priority Data
May 27, 2015 (KR) .................. 10-2015-0073562

(51) Int. Cl.
*A61B 6/00* (2006.01)
*G06K 9/52* (2006.01)
*G06T 5/00* (2006.01)
*G06T 5/50* (2006.01)

(52) U.S. Cl.
CPC .......... *A61B 6/5205* (2013.01); *A61B 6/4035* (2013.01); *A61B 6/482* (2013.01); *A61B 6/502* (2013.01); *G06K 9/52* (2013.01); *G06T 5/009* (2013.01); *G06T 5/50* (2013.01); *G06T 2207/10116* (2013.01); *G06T 2207/20016* (2013.01); *G06T 2207/20221* (2013.01); *G06T 2207/30004* (2013.01)

(58) Field of Classification Search
CPC .. G06K 9/00134; G02B 21/16; G02B 21/008; G02B 21/361; G02B 21/0076; G01N 21/6452; Y10T 29/49826
USPC ....................................................... 382/100
See application file for complete search history.

(56) References Cited

U.S. PATENT DOCUMENTS

| | | | |
|---|---|---|---|
| 9,836,830 B2 * | 12/2017 | Naito | .................. G01N 23/046 |
| 2010/0091943 A1 | 4/2010 | Kang et al. | |
| 2011/0123086 A1 | 5/2011 | Nie et al. | |
| 2014/0119507 A1 | 5/2014 | Oh et al. | |

* cited by examiner

*Primary Examiner* — Amandeep Saini
(74) *Attorney, Agent, or Firm* — Sughrue Mion, PLLC

(57) ABSTRACT

An X-ray apparatus includes an image separator configured to separate an X-ray image of an object into material images representing materials in the object; a parameter determiner configured to determine a width of a material of interest (MOI) based on the material images, and determine an enhancement parameter configured to enhance contrast of the MOI according to the width of the MOI; and an image enhancer configured to separate the X-ray image into detailed images respectively including spatial frequencies of different frequency bands, enhance each of the detailed images according to the enhancement parameter, and synthesize the enhanced detailed images to generate an enhanced image.

22 Claims, 10 Drawing Sheets

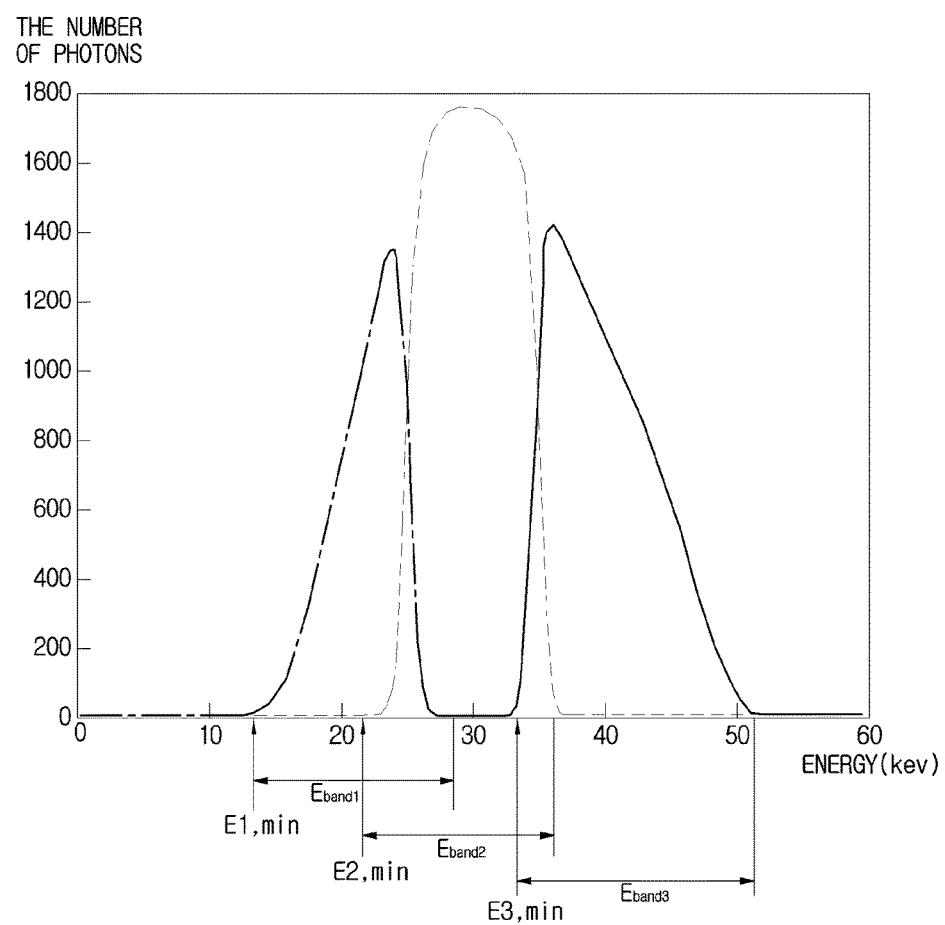

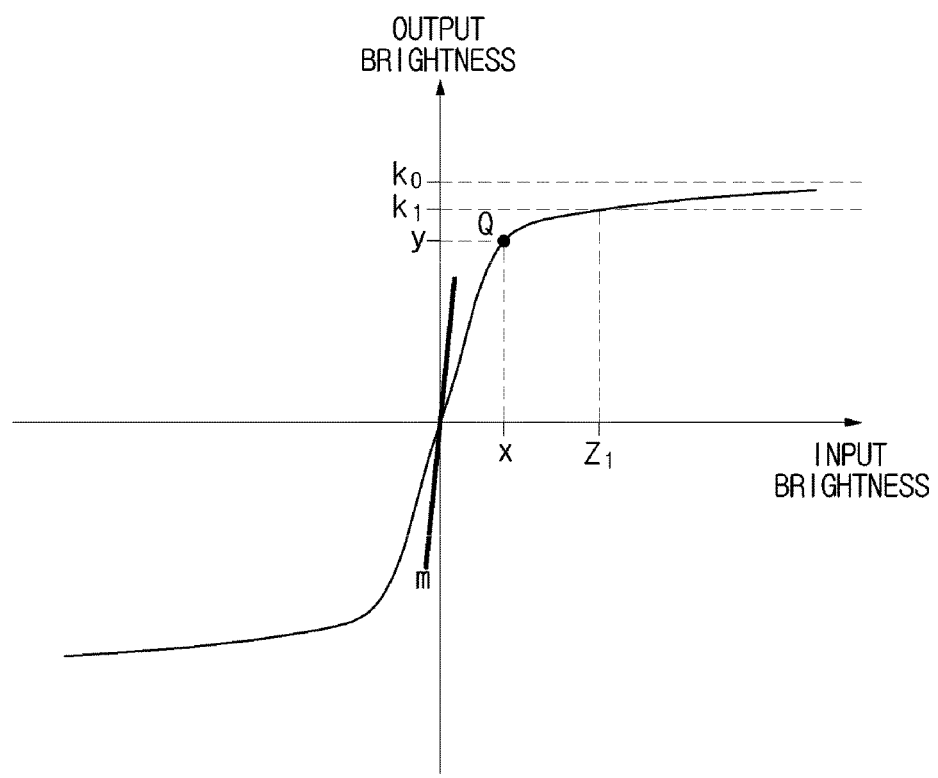

X-RAY APPARATUS AND CONTROL METHOD FOR THE SAME

CROSS-REFERENCE TO RELATED APPLICATION

This application claims priority to Korean Patent Application No. 10-2015-0073562, filed on May 27, 2015 in the Korean Intellectual Property Office, the disclosure of which is incorporated herein by reference in its entirety.

BACKGROUND

1. Field

Exemplary embodiments relate to an X-ray apparatus that radiates X-rays to a subject and generates images of an inside thereof, and to a control method for the same.

2. Description of the Related Art

X-ray apparatuses are apparatuses which can radiate X-rays to an object and obtain an internal image of the object using the X-rays that passed through the object. Since transmittance of X-rays differs based on characteristics of a material forming the object, it is possible to detect the intensity or strength of the X-rays that passed through the object to generate an image of an internal structure of the object.

The X-ray apparatus can perform an image processing process in order to convert the X-rays that passed through the object into an image which can be displayed on a display. For example, an X-ray apparatus can determine the number of pixels of an X-ray image or remove a noise other than information about an inside structure of an object based on X-rays that passed through the object.

As another example of the image processing process, an X-ray apparatus can enhance contrast between a plurality of materials forming an object. Thereby, the X-ray apparatus can provide users with enhanced X-ray images in which the inside of the object is recognized more clearly.

SUMMARY

Therefore, it is an aspect of the exemplary embodiments to provide an X-ray apparatus, which provides an enhanced image in which contrast is enhanced according to an enhancement parameter determined through material separation, and a control method for the same.

Additional aspects will be set forth in part in the description which follows and, in part, will be obvious from the description, or may be learned by practice of the exemplary embodiments.

According to an aspect of an exemplary embodiment, there is provided an X-ray apparatus including an image separator configured to separate an X-ray image of an object into material images representing materials in the object; a parameter determiner configured to determine a width of a material of interest (MOI) based on the material images, and determine an enhancement parameter configured to enhance contrast of the MOI according to the width of the MOI; and an image enhancer configured to separate the X-ray image into detailed images respectively including spatial frequencies of different frequency bands, enhance each of the detailed images according to the enhancement parameter, and synthesize the enhanced detailed images to generate an enhanced image.

The parameter determiner may be configured to determine the enhancement parameter for each of the detailed images and further enhance a detailed image having a spatial frequency of a band corresponding to the width of the MOI, among the detailed images, based on the enhancement parameter of the detailed image having the spatial frequency of the band corresponding to the width of the MOI.

The image enhancer may be configured to determine an enhancement function using the enhancement parameter, and enhance each of the detailed images according to the determined enhancement function.

The parameter determiner may be configured to determine the enhancement parameter as including at least one of an initial slope, coordinates of an inflection point, a convergence value, and a rate of convergence of the enhancement function.

The parameter determiner may be configured to increase the initial slope of the enhancement function applied to a detailed image of a high frequency among the detailed images, as the width of the MOI is decreased.

The parameter determiner may be configured to decrease an x-coordinate of the inflection point of the enhancement function applied to a detailed image of a high frequency among the detailed images, as the width of the MOI is decreased.

The parameter determiner may be configured to increase a y-coordinate of the inflection point of the enhancement function applied to a detailed image of a high frequency among the detailed images, as the width of the MOI is decreased.

The parameter determiner may be configured to increase the convergence value of the enhancement function applied to a detailed image of a high frequency among the detailed images, as the width of the MOI is decreased.

The parameter determiner may be configured to increase the rate of convergence of the enhancement function applied to a detailed image of a high frequency among the detailed images, as the width of the MOI is decreased.

The parameter determiner may be configured to determine the enhancement parameter of a detailed image having a preset frequency band among the detailed images so that the enhanced image has a preset target brightness.

The parameter determiner may be configured to increase a convergence value of an enhancement function applied to a detailed image having the preset frequency band among the detailed images, as the preset target brightness is increased.

The parameter determiner may be configured to decrease an x-coordinate of an inflection point of an enhancement function applied to a detailed image having the preset frequency band among the detailed images, as the preset target brightness is increased.

The X-ray apparatus may further include an image synthesizer configured to synthesize X-ray images corresponding to different energy bands and provide the synthesized X-ray images to the image enhancer, wherein the X-ray image of the object includes the X-ray images corresponding to the different energy bands.

The parameter determiner may be configured to determine the width of the MOI based on a number of pixels counted in a predetermined direction from an area in which the MOI is displayed in the material images.

According to an aspect of another exemplary embodiment, there is provided a control method for an X-ray apparatus, the control method including: separating an X-ray image of an object into material images representing materials in the object; determining a width of a material of interest (MOI) based on the material images; determining an enhancement parameter for enhancing contrast of the MOI according to the width of the MOI; separating the X-ray image into detailed images respectively having spatial frequencies of different frequency bands; enhancing each of the detailed images according to the enhancement parameter; and synthesizing the enhanced detail images to generate an enhanced image.

The determining of the enhancement parameter may include determining the enhancement parameter for each of the plurality of detailed images and further enhancing one of the detailed images having a spatial frequency of a band corresponding to the width of the MOI, among the detailed images, based on the enhancement parameter of the one detailed image.

The enhancing of the detailed images may include: determining an enhancement function representing enhanced contrast with respect to a change in contrast of the detailed images using the enhancement parameter; and enhancing each of the detailed images according to the determined enhancement function.

The determining of the enhancement parameter may include determining the enhancement parameter as including at least one of an initial slope, coordinates of an inflection point, a convergence value, and a rate of convergence of the enhancement function.

The determining of the enhancement parameter may include increasing the initial slope of the enhancement function applied to a detailed image of a high frequency among the detailed images, as the width of the MOI is decreased.

The determining of the enhancement parameter may include decreasing an x-coordinate of the inflection point of the enhancement function applied to a detailed image of a high frequency among the detailed images, as the width of the MOI is decreased.

The determining of the enhancement parameter may include increasing a y-coordinate of the inflection point of the enhancement function applied to a detailed image of a high frequency among the detailed images, as the width of the MOI is decreased.

The determining of the enhancement parameter may include increasing a convergence value of the enhancement function applied to a detailed image of a high frequency among the detailed images, as the width of the MOI is decreased.

The determining of the enhancement parameter may include increasing a rate of convergence of the enhancement function applied to a detailed image of high frequency among the detailed images, as the width of the MOI is decreased.

The determining of the enhancement parameter may include determining the enhancement parameter of a detailed image having a preset frequency band among the detailed images so that the enhanced image has a preset target brightness.

The determining of the enhancement parameter may include increasing a convergence value of an enhancement function applied to a detailed image having the preset frequency band among the detailed images, as the preset target brightness is increased.

The determining of the enhancement parameter may include decreasing an x-coordinate of an inflection point of the enhancement function applied to a detailed image having the preset frequency band among the detailed images, as the preset target brightness is increased.

The control method may further include synthesizing X-ray images corresponding to different energy bands into a synthesized X-ray image, wherein the X-ray image of the object has the X-ray images corresponding to the different energy bands, wherein the separating of the X-ray image into the detailed images comprises separating the synthesized X-ray image into the detailed images having spatial frequencies of the different frequency bands.

The determining of the width of the MOI may include determining the width of the MOI based on a number of pixels counted in a predetermined direction from an area in which the MOI is displayed in the material images.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIG. 5A is a graph showing an X-ray spectrum for each energy band.

FIG. 6 is an exemplified view showing an enhancement function graph according to an exemplary embodiment;

DETAILED DESCRIPTION

Figure 1:
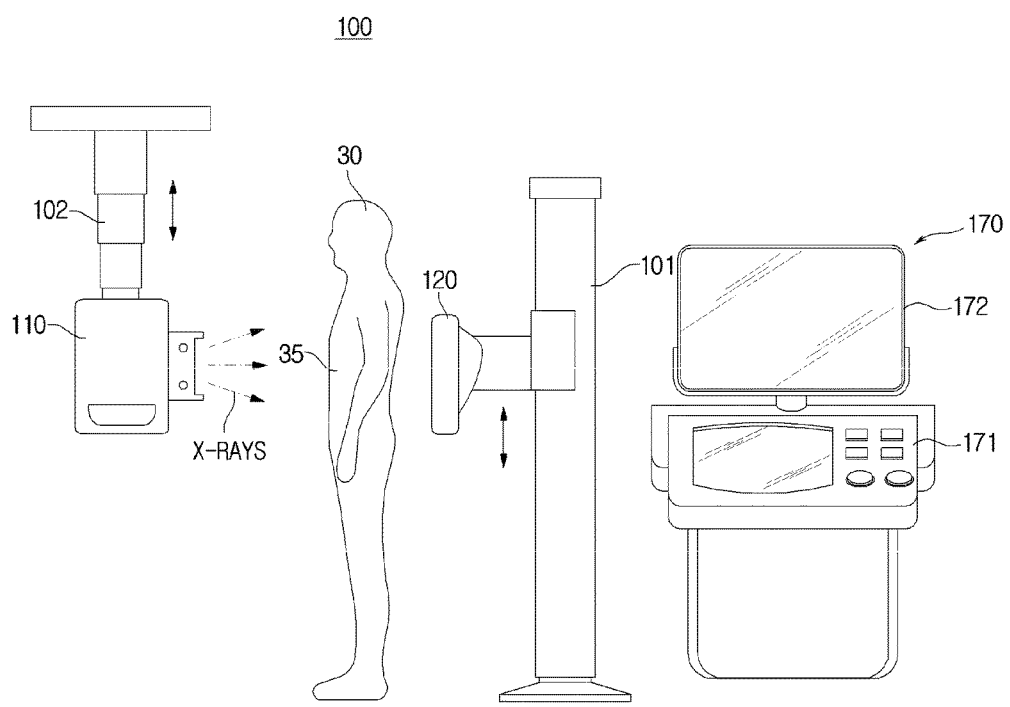
FIG. 1 is a diagram illustrating an exterior of an X-ray apparatus according to an exemplary embodiment.

Reference will now be made in detail to the exemplary embodiments, examples of which are illustrated in the accompanying drawings, wherein like reference numerals refer to like elements throughout.

Hereinafter, exemplary embodiments of an X-ray apparatus and a control method for the same will be described in detail below with reference to the accompanying drawings.

Figure 2:
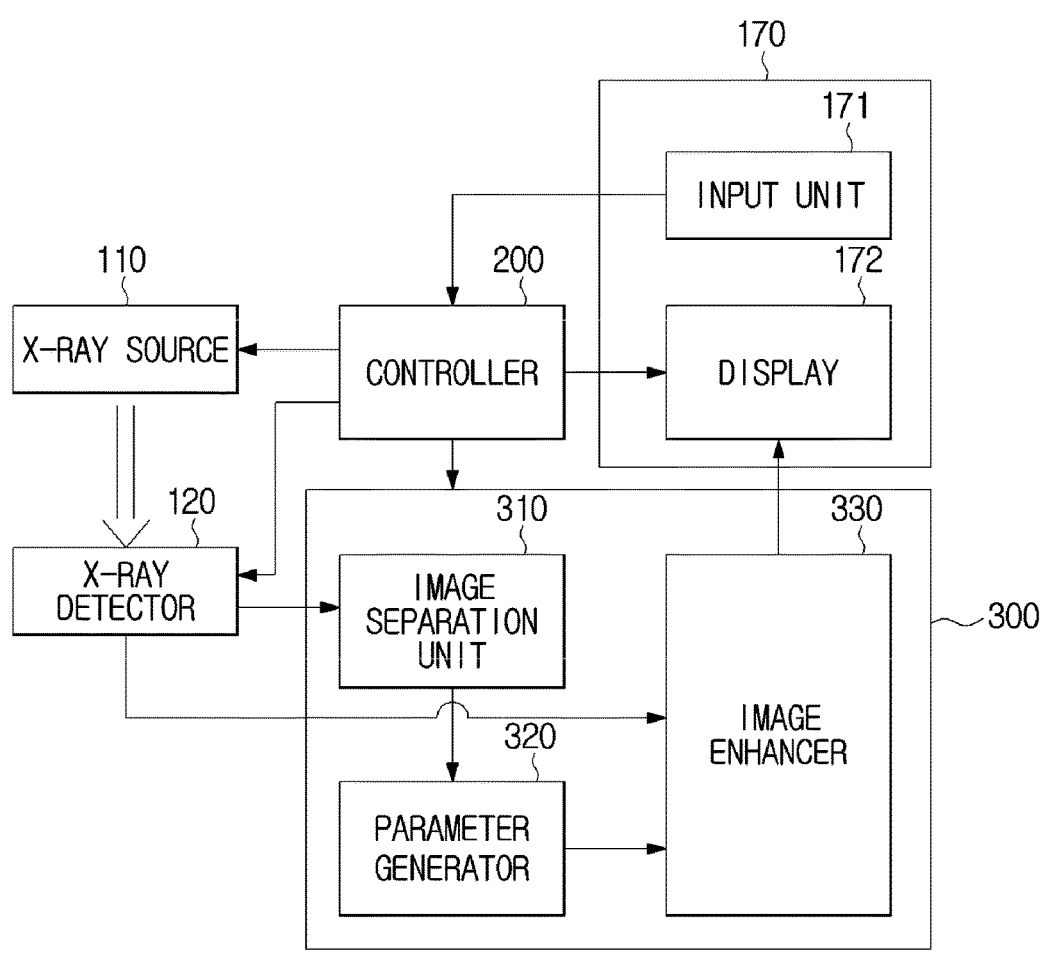
FIG. 2 is a control block diagram of the X-ray apparatus according to an exemplary embodiment.
Figure 3:
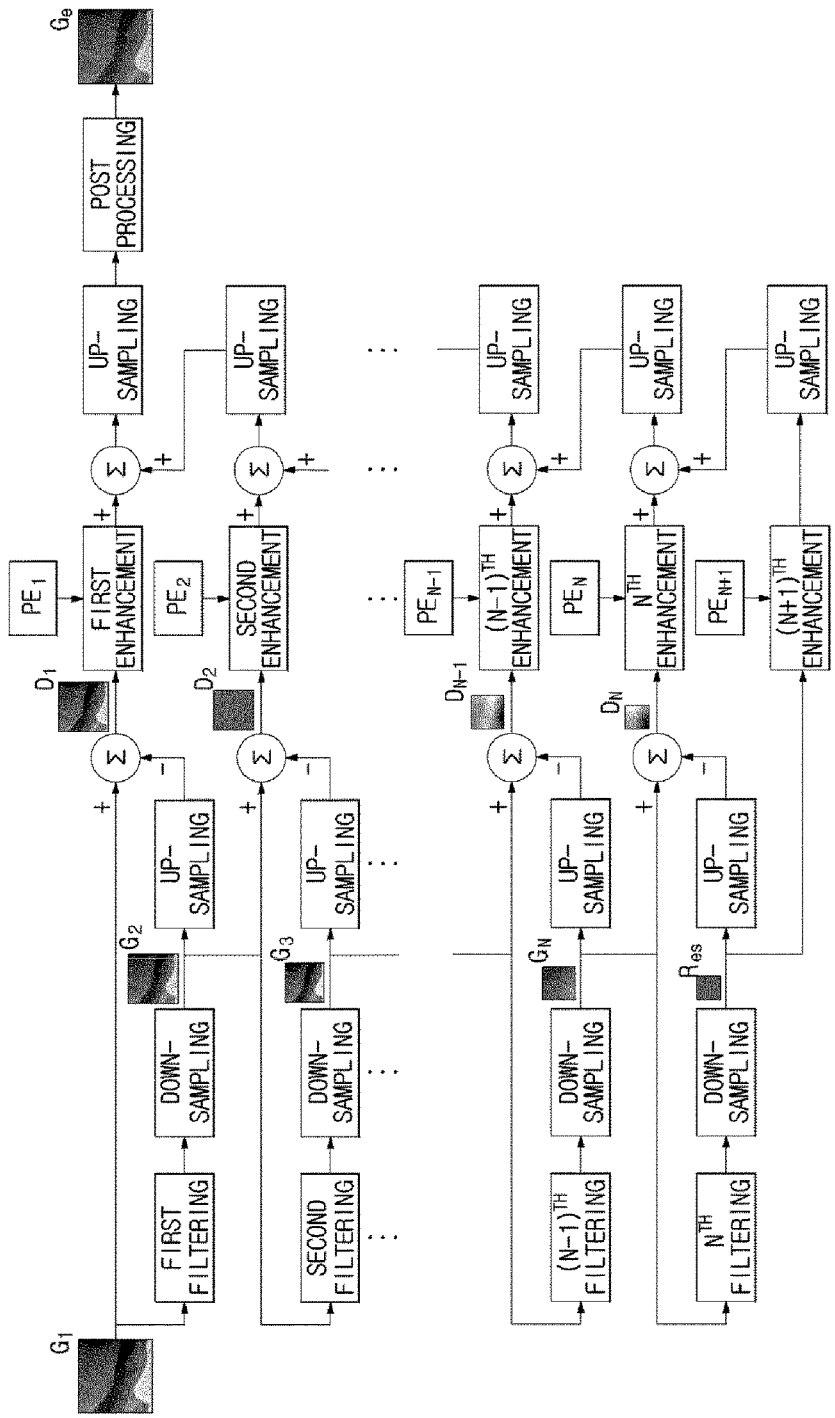
FIG. 3 is a diagram for describing an operation of an image processor according to an exemplary embodiment.

FIG. 1 is a diagram illustrating an exterior of an X-ray apparatus according to an exemplary embodiment, FIG. 2 is a control block diagram of the X-ray apparatus according to an exemplary embodiment, and FIG. 3 is a diagram for describing an operation of an image processor according to an exemplary embodiment.

Referring to FIGS. 1 and 2, an X-ray apparatus 100 according to an exemplary embodiment may include an X-ray source 110 which generates and radiates X-rays, an X-ray detector 120 which detects the radiated X-rays and obtains an X-ray image, a controller 200 which controls an operation of the X-ray source and the X-ray detector, an image processor 300 which performs an image processing process of the X-ray image obtained by the X-ray detector, and a host unit 170 (e.g., host) for a user which provides information to a user and receives input control commands from the user.

The X-ray source 110 may generate X-rays to obtain an X-ray image of an object, and may radiate the generated X-rays to a subject. Here, the subject 30 may be a body of a human or animal, but it is not limited thereto, and the subject may be any one of which an internal structure can be made as an image using the X-ray apparatus. In addition, an object 35 refers to a portion which is an object inside the subject diagnosed using the X-ray apparatus, that is, an X-ray imaging region. FIG. 1 shows an exemplified abdomen of the object, but exemplary embodiments are not limited thereto.

The X-ray source 110 may include an X-ray tube which generates X-rays. When a high voltage is applied between positive and negative electrodes of the X-ray tube, thermoelectrons are accelerated and collide with a target material of the positive electrode. Thereby, the X-rays may be generated. Here, the voltage applied between the positive and negative electrodes is referred to as a tube voltage, and a level thereof may be indicated as a peak value kvp. As the tube voltage is increased, the speed of the thermoelectrons is increased, and as a result, energy (photon energy) of X-rays generated by the thermoelectrons colliding with the target material may be increased. In addition, a filter may be disposed in an irradiating direction of the X-rays to control the energy of the X-rays. Specifically, a filter which filters X-rays in a specific frequency band may be disposed at a front or rear of a window thereof to filter the X-rays in a specific energy band. In addition, the tube current introduced into an X-ray source 110 may be changed to control the energy of the radiated X-rays. Here, the tube current refers to a current which flows in the X-ray tube, and when the tube current is increased, an X-ray dose (the number of X-ray photons) may be increased.

As illustrated in FIG. 1, the X-ray source 110 may be fixed to a ceiling and installed to be vertically movable. Specifically, the X-ray source 110 may be connected to a post frame 102 of which a plurality of posts are telescopically fixed to the ceiling. Since the X-ray source 110 vertically moves according to an operation of the post frame, a position of the X-ray source 110 may correspond to a position of the object. However, FIG. 1 simply shows an exemplary embodiment in which the X-ray source 110 is provided, and the X-ray source 110 may be variously implemented according to exemplary embodiments based on various technical aspects by which X-rays are radiated to the object.

The X-ray detector 120 is disposed to be opposite the X-ray source 110 and the object is interposed therebetween, and the X-ray detector 120 may detect X-rays which are radiated from the X-ray source 110 and pass through the object. In addition, the X-ray detector 120 may generate an X-ray image based on the detected X-rays. When an X-ray detector 120 has a two dimensional array structure having a plurality of pixels, the X-ray detector 120 may convert the detected X-rays for each pixel into electrical signals and generate an X-ray image of the object. Generally, an X-ray detector 120 may be classified according to a method of converting the detected X-rays into electrical signals, a method of obtaining X-ray data, etc.

First, an X-ray detector 120 may be classified into a direct conversion method and an indirect conversion method according to a method of converting X-rays into electrical signals. In the direct conversion method, when X-rays are radiated, electron-hole pairs are temporarily generated inside a light-receiving element, and electrons move to a positive electrode and holes move to a negative electrode due to an electric field applied to both ends of the light-receiving element, and an X-ray detector 120 converts this movement into an electrical signal. In the direct conversion method, a-Se, CdZnTe, HgI2, PbI2 or the like is used as a material of the light-receiving element. In the indirect conversion method, a scintillator is provided between a light-receiving element and an X-ray source 110. The scintillator reacts with X-rays radiated from the X-ray source 110 and emits photons having a wavelength of a visible light range. The light-receiving element detects the photons emitted from the scintillator and converts the photons into an electrical signal. In the indirect conversion method, a-Si or the like is used as a material of the light-receiving element, and a thin film GADOX scintillator, a micro columnar scintillator, a needle-shaped CSI $(T_1)$ scintillator or the like may be used as the scintillator.

In addition, according to a method of obtaining X-ray data, an X-ray detector 120 may be classified into a charge integration mode in which charges are stored for a predetermined time and then a signal is obtained therefrom and a photon counting mode in which photons having a higher energy than a threshold energy are counted whenever a signal is generated by a single X-ray photon.

As illustrated in FIG. 1, the X-ray detector 120 may be installed at a stand 101 in a sliding manner to be vertically movable. Thereby, similar to the X-ray source 110, the X-ray detector 120 may be vertically moved to a position corresponding to a position of the object 35 by the sliding manner. However, FIG. 1 simply shows an exemplary embodiment in which the X-ray detector 120 is provided, and the X-ray detector 120 may be variously implemented according to other techniques by which X-rays are radiated to the object.

The controller 200 may control the X-ray apparatus according to control commands input through an input unit 171 (e.g., inputter) or an internal algorithm thereof. For example, the controller 200 may control a tube voltage or a tube current applied to the X-ray source 110 to change the energy of X-rays radiated to the object. In addition, when the X-ray detector 120 is implemented in the photon counting mode, the controller 200 may determine the threshold energy of the X-ray detector 120. In addition, in order to obtain anatomical information of the object, the controller 200 may move the X-ray source 110 and the X-ray detector 120 to a position corresponding to a position of the object. In addition, the controller 200 may control an image processing method of the image processor 300 in a manner to be described below, or control an X-ray image display method of a display unit 172. The controller 200 may be implemented in hardware such as a microprocessor, but may also be implemented as software.

The host unit 170 may include the input unit 171 for inputting control commands by a user, and the display unit 172 (e.g., display) configured to display a user interface which provides an X-ray image processed by the image processor 300 and X-ray imaging related information.

A switch, a keyboard, a trackball, or a touch screen may be included according to an exemplary embodiment of the input unit 171, but implementation is not limited thereto within the technical aspect in which control commands are input by a user.

The display unit 172 may be connected to the image processor 300 to be described below, and may display an X-ray image processed by the image processor 300. At this time, the X-ray image displayed by the display unit 172 may be a still image at a specific time, or may be a moving image including a plurality of frame images. In addition, the display unit 172 may provide the user interface related to X-ray imaging. For example, the display unit 172 may display a menu or guide information required for X-ray imaging.

The display unit 172 may be implemented by a cathode ray tube (CRT), a liquid crystal display (LCD), an electroluminescence display (ELD), a field emission display (FED), a plasma display, a thin film transistor-LCD (TFT-LCD), or an organic light emitting diode (OLED), but it is not limited thereto.

The image processor 300 may process an X-ray image generated by the X-ray detector 120 and provide the X-ray image to the display unit 172. Specifically, the image processor 300 may include an image enhancer 330 which enhances an X-ray image generated by the X-ray detector 120 to generate an enhanced image of which contrast is enhanced.

To this end, the image enhancer 330 may perform a multi-scale enhancement on the X-ray image. The multi-scale enhancement may refer to a method which separates an X-ray image into a plurality of scale images having spatial frequencies of bands different from each other, and enhances each of the plurality of scale images. Since each of the plurality of scale images includes a shape or feature point corresponding to each spatial frequency band, the image processor 300 may optionally or comprehensively enhance the plurality of scale images according to a shape or feature point required to be enhanced.

Particularly, the image enhancer 330 may separate an X-ray image into Laplacian pyramids during multi-scale enhancement. The plurality of scale images described above form a Gaussian pyramid, and the Laplacian pyramid may include a plurality of detailed images indicating differences of the adjacent scale images in the Gaussian pyramid. Similar to the scale image, since each of the plurality of detailed images includes a shape or feature point corresponding to a spatial frequency band, the image processor 300 may optionally or comprehensively enhance the plurality of detailed images according to a shape or feature point required to be enhanced. In addition, since the detailed image forming the Laplacian pyramid has a smaller data size than the scale image, when the multi-scale enhancement is performed using the detailed image, an image processing time may be reduced. In addition, since an image of the image enhancer is enhanced and synthesized, the enhanced image may be easily generated.

FIG. 3 shows an exemplary embodiment of a method of using a Laplacian pyramid among multi-scale enhancement methods. The image enhancer 330 separates an original X-ray image into Laplacian pyramids, and each of a plurality of detailed images is enhanced and synthesized, and then, one enhanced image may be generated.

Specifically, the image enhancer 330 performs a first filtering on a first scale image $G_1$, that is, an original X-ray image, to remove a first frequency band and down-samples the result thereof, and thus, a second scale image $G_2$ may be generated. In addition, the image enhancer 330 performs a second filtering on the second scale image $G_2$ to remove a second frequency band and down-samples the result thereof, and thus, a third scale image $G_3$ may be generated. At this time, the second frequency band is adjacent to the first frequency band, and may refer to a frequency band lower than the first frequency band. In a similar manner, the image enhancer 330 performs an $(N-1)^{th}$ filtering on an $(N-1)^{th}$ scale image $G_{N-1}$ to remove an $(N-1)^{th}$ frequency band, and down-samples the result thereof, and thus, an $N^{th}$ scale image $G_N$ may be generated. At this time, the $(N-1)^{th}$ frequency band is adjacent to the $(N-2)^{th}$ frequency band, and may refer to a frequency band lower than the $(N-2)^{th}$ frequency band. Finally, the image enhancer 330 performs an $N^{th}$ filtering on an $N^{th}$ scale image $G_N$ to remove an $N^{th}$ frequency band, and down-samples the result thereof, and thus, a baseband image Res may be generated. At this time, the $N^{th}$ N frequency band may refer to any frequency band lower than the $(N-1)^{th}$ frequency band.

The first scale image to the $N^{th}$ scale image and the baseband image Res generated from the processes described above may form a Gaussian pyramid. The image enhancer 330 may obtain a plurality of detailed images which are difference images of adjacent scale images to generate a Laplacian pyramid.

Referring to FIG. 3, the image enhancer 330 may up-sample the second scale image $G_2$ so that the up-sampled second scale image $G_2$ has the same scale as the first scale image $G_1$. Then, the image enhancer 330 may calculate a difference between the first scale image $G_1$ and the up-sampled second scale image $G_2$ to obtain a first detail image $D_1$ (e.g., detailed image). Since the second scale image is an image in which the first frequency band is removed from the first scale image, the first detailed image $D_1$ may refer to an image corresponding to only the first frequency band. In addition, the image enhancer 330 may up-sample the third scale image $G_3$ so that the up-sampled third scale image $G_3$ has the same scale as the second scale image $G_2$. Then, the image enhancer 330 may calculate a difference between the second scale image $G_2$ and the up-sampled third scale image $G_3$ to obtain a second detailed image $D_2$. Since the third scale image is an image in which the second frequency band is removed from the second scale image, the second detailed image $D_2$ may refer to an image corresponding to only the second frequency band. In a similar manner, the image enhancer 330 may up-sample an $N^{th}$ scale image $G_N$ so that the up-sampled $N^{th}$ scale image $G_N$ has the same scale as the $(N-1)^{th}$ scale image $G_{N-1}$. Then, the image enhancer 330 may calculate a difference between the $(N-1)^{th}$ scale image $G_{N-1}$ and the up-sampled $N^{th}$ scale image $G_N$ to obtain an $(N-1)^{th}$ detailed image $D_{N-1}$. Since the $N^{th}$ scale image is an image in which the $(N-1)^{th}$ frequency band is removed from the $(N-1)^{th}$ scale image, the $(N-1)^{th}$ detailed image $D_{N-1}$ may refer to an image corresponding to only the $(N-1)^{th}$ frequency band. Finally, the image enhancer 330 may up-sample the baseband image Res so that the up-sampled baseband image Res has the same scale as that of the $N^{th}$ scale image $G_N$. Then, the image enhancer 330 may calculate a difference between the $N^{th}$ scale image $G_N$ and the up-sampled baseband image Res to obtain an $N^{th}$ detailed image $D_N$. Since the baseband image is an image in which the $N^{th}$ frequency band is removed from the $N^{th}$ scale image, the $N^{th}$ detailed image $D_N$ may refer to an image corresponding to only the $N^{th}$ frequency band.

The first detailed image to the $N^{th}$ detailed image and the baseband image generated through the processes described above may form a Laplacian pyramid. A plurality of detailed images to be described below may include the first detailed image to the $N^{th}$ detailed image and the baseband image forming a Laplacian pyramid.

Since each of the plurality of detailed images forming the Laplacian pyramid corresponds to only a corresponding frequency band, each of the plurality of detailed images may include a shape or feature point different from each other. Thus, the image enhancer 330 may enhance each of the plurality of detailed images in consideration of the shape or feature point required to be enhanced. Referring to FIG. 3, the image enhancer 330 may perform a first enhancement on the first detailed image $D_1$. Here, the first enhancement refers to performing an enhancement using a first enhancement function determined by a first enhancement parameter $PE_1$, and the enhancement function may refer to an output contrast function with respect to input contrast. In addition, the image enhancer 330 may perform a second enhancement on the second detailed image $D_2$ using a second enhancement function determined by a second enhancement parameter $PE_2$. In a similar manner, the image enhancer 330 may perform an $(N-1)^{th}$ enhancement on the $(N-1)^{th}$ detailed image $D_{N-1}$ using an $(N-1)^{th}$ enhancement function determined by an $(N-1)^{th}$ enhancement parameter $PE_{N-1}$, and may perform an $N^{th}$ enhancement on the $N^{th}$ detailed image $D_N$ using an $N^{th}$ enhancement function determined by an $N^{th}$ enhancement parameter $PE_N$. Finally, the image enhancer 330 may perform an $(N+1)^{th}$ enhancement on the baseband image Res using an $(N+1)^{th}$ enhancement function determined by an $(N+1)^{th}$ enhancement parameter $PE_{N+1}$. Generally, the baseband image Res includes brightness information of the original image $G_1$, and the image enhancer 330 may determine the brightness of an enhanced image GE finally generated through the $(N+1)^{th}$ enhancement.

Finally, the image enhancer 330 may synthesize a plurality of enhanced detailed images to generate one enhanced image. Since each of the plurality of detailed images has a natural frequency band, the plurality of detailed images may be synthesized to restore an enhanced image having the same frequency band as the original X-ray image. Referring to FIG. 3, the image enhancer 330 may up-sample the N+1-th enhanced baseband image Res so that the $(N+1)^{th}$ enhanced baseband image Res has the same scale as that of the $N^{th}$ detailed image, and may synthesize the $(N+1)^{th}$ enhanced baseband image Res and the $N^{th}$ enhanced $N^{th}$ detailed image. In a similar manner, the image enhancer 330 may up-sample an image to have the same scale as that of an adjacent detailed image, synthesize the up-sampled image and the adjacent detailed image, and perform a post process, and thus, an enhanced image having enhanced contrast may be generated.

As described above, the image enhancer 330 may use a plurality of enhancement parameters to enhance a plurality of detailed images. The plurality of enhancement parameters may be differently applied according to an object to which X-rays are radiated, and may be determined in consideration of a shape or feature point included in each of the plurality of detailed images. For example, when X-rays are radiated to a human breast, a plurality of enhancement parameters may be determined to enhance the contrast of mammary gland tissues and fat tissues of the breast. Particularly, the plurality of enhancement parameters may be determined in consideration of a shape or feature point of the fat and mammary gland tissues included in an X-ray image of the breast generated by the X-ray detector 120 and a plurality of detailed images separated from the X-ray image.

At this time, each subject, that is, a person, may have a different ratio of materials forming a breast. When the ratio of materials forming the breast or a tissue shape of the breast is in an abnormal range, an X-ray image of the breast obtained through an X-ray apparatus may be distorted. Specifically, an X-ray image may be brighter or darker than a brightness state in which an X-ray diagnosis is possible in normal. In addition, the contrast of the X-ray image may be out of the range at which the X-ray diagnosis is normally possible, and thus, identification of breast tissues may be vague.

In addition, when X-rays are radiated to the same object of a subject in a different imaging environment, an X-ray image having a different contrast may be obtained. In this case, when the X-ray image is enhanced using the same enhancement parameter, an enhanced image finally generated may also have a different contrast according to the imaging environment. For example, when X-ray imaging is performed on a breast of the same person in different X-ray radiating directions, X-ray images having a different contrast between fat tissues and mammary gland tissues may be obtained. When the X-ray images of the breast are enhanced by applying the same enhancement parameter thereon, the enhanced images may also have a different contrast between the fat tissues and the mammary gland tissues. As a result, a user may have difficulty finding corresponding points between a plurality of enhanced images having different contrasts, and thus, X-ray diagnosis may lead to inconvenience.

Thus, it may be required that anatomical information of an independent object is obtained from contrast of an X-ray image, an enhancement parameter is determined based on the information obtained in this manner, and thereby, the X-ray image having a contrast independent of a ratio of materials of the object or an X-ray imaging environment is provided.

According to an exemplary embodiment, there is provided an X-ray apparatus which obtains a width of a material of interest (MOI) through a material image separated from an X-ray image, and determines an enhancement parameter based on the obtained width. Hereinafter, first, a method of obtaining a width of an MOI through material separation will be described, and a method of determining an enhancement parameter based on the obtained width in this manner will be described.

When X-rays are radiated to an object from an X-ray source, a degree of attenuation of the X-rays may be changed according to a material inside the object and an energy band of the radiated X-rays. Here, the degree of attenuation of the X-rays is numerically referred to as an attenuation coefficient. The attenuation coefficient may be changed according to a material inside an object.

Figure 4:
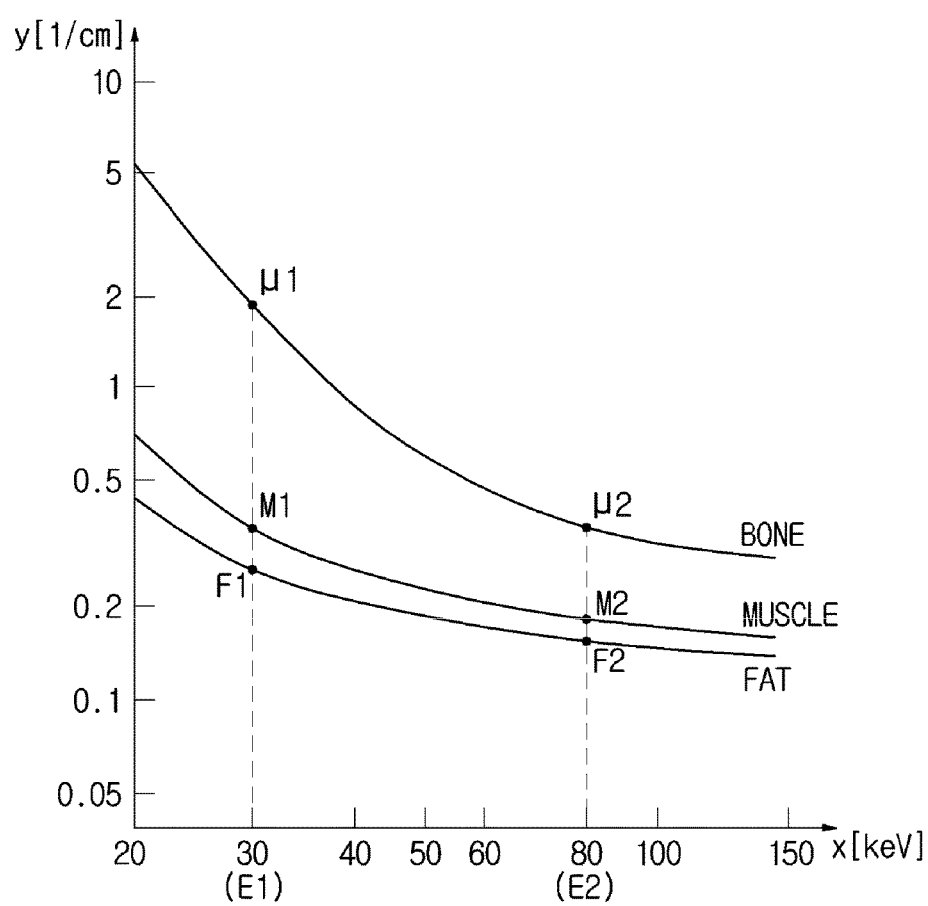
FIG. 4 is a graph showing the relation between energy and an attenuation coefficient for each material inside an object.

FIG. 4 is a graph showing the relation between energy and an attenuation coefficient for each material inside an object. An X axis refers to photon energy radiated to an object, and a Y axis refers to an attenuation coefficient.

As shown from a graph in FIG. 4, a curve indicating an attenuation coefficient of a bone is positioned above a curve indicating an attenuation coefficient of soft tissue (muscle or fat). Specifically, when X-rays of the same energy level, for instance, $E_1$, are radiated, an attenuation coefficient $\mu_1$ of the bone is greater than an attenuation coefficient $M_1$ of the muscle, and the attenuation coefficient $M_1$ of the muscles is greater than an attenuation coefficient $F_1$ of the fat. That is, different materials inside an object have different attenuation coefficients, and an attenuation coefficient increases as an atomic number and a degree of density is higher.

In addition, the attenuation coefficient is changed according to an energy band of radiated X-rays. From the graph in FIG. 4, when X-rays having energy bands of $E_1$ and $E_2$ are radiated to the bone which is a material inside the object, the attenuation coefficient $\mu_1$ at a lower energy band $E_1$ is greater than an attenuation coefficient $\mu_2$ at a higher energy band $E_2$. It may be determined that, when the material inside the object is muscle or fat, the attenuation coefficients $M_1$ or $F_1$ when a low energy band $E_1$ is radiated is respectively greater than the attenuation coefficients $M_2$ or $F_2$ when a high energy band $E_2$ is radiated. That is, as an energy band of X-rays radiated to an object is decreased, an attenuation coefficient is increased.

The attenuation coefficient may be expressed according to the following Equation 1.

$$I = I_0 \cdot e^{-\mu(E) \cdot T} \quad \text{[Equation 1]}$$

Here, $I_0$ denotes an intensity of X-rays radiated to a material, I denotes an intensity of X-rays that passed through the material, and μ(E) denotes an attenuation coefficient of the material with respect to X-rays having energy E. T denotes a thickness of the material through which X-rays pass.

According to Equation 1, as an attenuation coefficient is increased (that is, an atomic number and density of a material is higher or an energy band of the radiated X-rays is lower) and a thickness of a material is greater, an intensity of the X-rays is decreased.

As shown from the graph in FIG. 4, since the difference of attenuation coefficients between materials is changed according to an intensity of energy, X-ray images having different energy bands are obtained, and when attenuation characteristics for materials at energy bands are used, each of the images, into which a material image is separated, is obtained from X-ray images having different energy bands. For example, when separated images corresponding to three materials are required to be obtained, X-ray images corresponding to energy bands $E_{band1}$, $E_{band2}$, and $E_{band3}$ different from each other may be obtained.

Figure 5B:
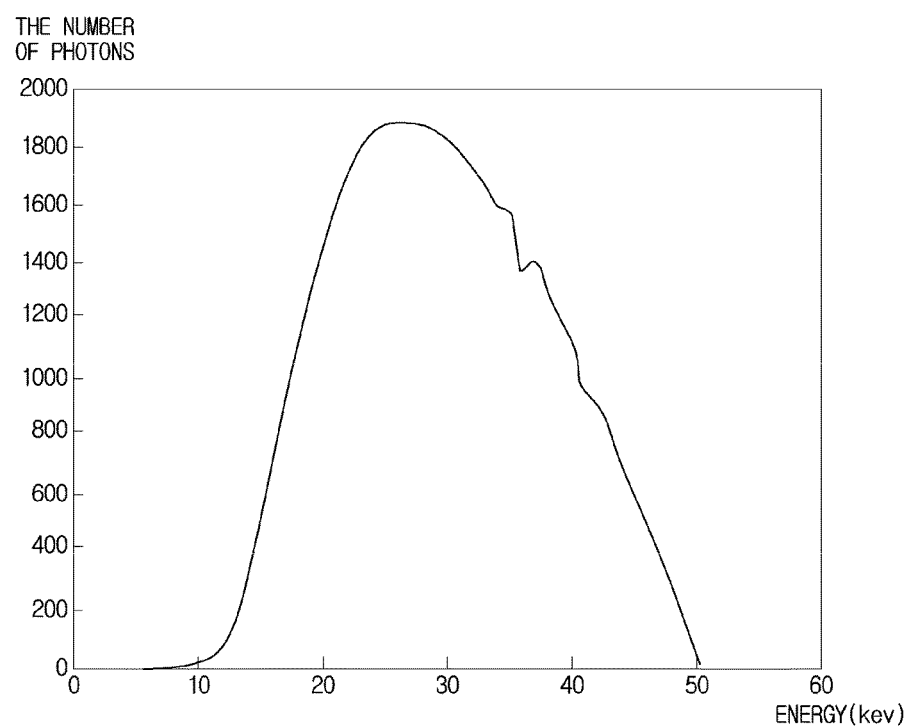
FIG. 5B is an exemplified graph showing an X-ray spectrum radiated from an X-ray source.

FIG. 5A is a graph showing an X-ray spectrum for each energy band, and FIG. 5B is an exemplified graph showing an X-ray spectrum radiated from an X-ray source 110. For the sake of convenience, vertical axes of graphs in FIG. 5A and FIG. 5B are referred to as the number of photons, but the vertical axes of the graphs may be replaced by intensity of X-rays.

Methods of obtaining X-ray images having different energy bands include a method in which the X-ray source 110 radiates X-rays having different energy bands a plurality of times and a method in which the X-ray source 110 radiates wideband X-rays having a plurality of energy bands once and the X-ray detector 120 detects the wideband X-rays and separates the wideband X-rays into respective energy bands. When the former method is applied to the X-ray apparatus, the X-ray source 110 radiates X-rays of $E_{band1}$, the X-ray detector 120 detects the X-rays and obtains an X-ray image corresponding to the $E_{band1}$. For $E_{band2}$, and $E_{band3}$, X-ray images are obtained using the same method as the $E_{band1}$.

When the latter method is applied to the X-ray apparatus, as illustrated in FIG. 5B, the X-ray source 110 radiates wideband X-rays including three energy bands once and the X-ray detector 120 detects the wideband X-rays and separates the wideband X-rays into respective energy bands. As illustrated in FIG. 5B, for example, the X-ray source 110 may generate and radiate X-rays having a lower energy limit of 10 keV and an upper energy limit of 50 keV. To this end, the X-ray source 110 may generate X-rays using a tube voltage of 50 kvp, and filter a low energy band (about 0 to 10 keV) to radiate the X-rays. At this time, an X-ray dose (the number of photons) indicating the y axis may be controlled by a tube current and an X-ray exposure time. In order to separate detected X-rays by energy bands, the X-ray detector 120 may be implemented in the photon counting mode. When electrons or holes generated from a single photon are input to the light-receiving element of the X-ray detector 120 and output in a voltage signal, a read circuit of the X-ray detector 120 may count the number of photons which generate a voltage greater than a preset threshold voltage. At this time, when a plurality of threshold voltages different from each other are preset, the read circuit may count the number of photons which have a voltage greater than each threshold voltage. As a result, the X-ray detector 120 may generate X-ray images for energy bands corresponding to threshold voltages based on the number of photons counted for each threshold voltages. For example, the X-ray detector 120 may generate X-ray images of three energy bands $E_{band1}$, $E_{band2}$, and $E_{band3}$ corresponding to three threshold voltages.

When X-ray images corresponding to a plurality of energy bands are generated by the X-ray detector 120, the image processor 300 may determine enhancement parameters using the X-ray images. Specifically, the image processor 300 may obtain anatomical information of an object independent of contrast of an X-ray image, that is, a width of an MOI, and may determine an enhancement parameter based thereon. To this end, the image processor 300 may further include an image separation unit 310 (e.g., image separator) which separates an X-ray image of an object generated by the X-ray detector 120 into a plurality of material images, and a parameter determination unit 320 (e.g., parameter determiner) which determines a width of an MOI from the plurality of material images and determines an enhancement parameter according to the width of the MOI.

The image separation unit 310 may separate a material image from an X-ray image corresponding to a plurality of energy bands input from the X-ray detector 120. According to an exemplary embodiment, when the number of types of materials to be separated is two, the image separation unit 310 may separate into two material images by performing two arithmetic operations in which the image separation unit 310 multiplies at least one of the X-ray images corresponding to two energy bands by a weight value and performs subtraction. This feature may be referred to as dual-energy X-ray absorptiometry.

For example, when materials required to be separated are a bone and soft tissue, an X-ray image corresponding to a lower energy band (hereinafter, referred to as a low energy X-ray image) may be multiplied by a predetermined weight value and the multiplied low energy X-ray image may be subtracted from an X-ray image corresponding to a higher energy band (hereinafter, referred to as a high energy X-ray image), and a soft tissue image may be obtained. That is, a vivid soft tissue image in which a bone image is removed may be obtained. On the contrary, high energy data may be multiplied by a predetermined weight value and the multiplied high energy data may be subtracted from low energy data, and a bone image may be obtained. That is, a vivid bone image in which a soft tissue image is removed may be obtained. Also, it is possible to respectively multiply low energy data and high energy data by appropriate weight values and perform subtraction, and to obtain a soft tissue image or a bone image. Using the method described above, the image separation unit 310 may separate an X-ray image corresponding to a plurality of energy bands into two material images of different motion properties such as those of the bone and soft tissue, and may generate a plurality of material images. As another example, when the number of types of materials required to be separated is three or more, the image separation unit may multiply respective X-ray data corresponding to three energy bands by an appropriate weight value and perform subtraction, and may separate the image frames into three or more types of images. For example, the image separation unit 310 may separate each image frame into three material images of different motion properties such as those of the bone and soft tissue, and may generate a plurality of material images. The X-ray apparatus according to an exemplary embodiment is not limited to types or the number of materials to be separated. In addition, a method of multiplying an image by a weight value and performing subtraction, and separating a material image, is only one of the methods capable of being used by the image separation unit 310, and a material image may also be separated using other methods.

When a material image is separated from an X-ray image, the parameter determination unit 320 may determine a width of an MOI from the material image. Here, the MOI may refer to a target material to be enhanced. For example, when a human breast is a target, a mammary gland may be an MOI. The parameter determination unit 320 may determine a width of an MOI using a material image of the MOI among a plurality of material images. Since the material image of the MOI is an image in which the MOI is separated from a plurality of materials of an object, the material image of the MOI may include anatomical information of the object independent of contrast of an X-ray image, that is, a width of the MOI. The parameter determination unit 320 may determine the number of pixels in a predetermined direction from an area in which the MOI is displayed in the material image as a width of the MOI. For example, the parameter determination unit 320 may determine the number of MOI image pixels, which are positioned in a direction perpendicular to a tangent line of an area in which an MOI is displayed in material images, as a width of the MOI. In addition, the parameter determination unit 320 may measure a width of an MOI according to various exemplary embodiments capable of being applied. For example, the parameter determination unit 320 may measure an average width of MOIs in a material image as a width of the MOI, and may determine a width at a predetermined position in an MOI as a width of the MOI. In addition, it is possible that the parameter determination unit 320 may also determine a minimum width or a maximum width in a material image as a width of an MOI.

After the width of an MOI is measured, the parameter determination unit 320 may determine an enhancement parameter according to the width of the MOI. As described above, the enhancement parameter may refer to a parameter which determines an enhancement function, and the enhancement function is an output contrast function after enhancing input contrast to be enhanced, and may be in a nonlinear curve shape.

Since each detailed image includes a different shape or feature point, and the image enhancer 330 enhances the detailed image in consideration of the shape or feature point, the parameter determination unit 320 may determine each enhancement parameter for each detailed image. Particularly, the parameter determination unit 320 may determine each enhancement parameter for each of a plurality of detailed images in order to further enhance a detailed image having a spatial frequency corresponding to a width of an MOI. Generally, as a detailed image has a high spatial frequency, the detailed image may include a shape of a material having a small width, and as a detailed image has a low spatial frequency, the detailed image may include a shape of a material having a great width. Thus, the parameter determination unit 320 determines a spatial frequency corresponding to a width of an MOI, and enhances a detailed image having the spatial frequency that is more than a remaining detailed image to increase a ratio of the detailed image having the spatial frequency corresponding to the width of the MOI in an enhanced image that is finally generated. Here, the number of detailed images having the spatial frequency corresponding to the width of the MOI may be one or a plurality. When the number of detailed images corresponding to a width of an MOI is a plurality, the parameter determination unit 320 may also enhance each of the plurality of detailed images corresponding to widths to varying degrees.

Hereinafter, a method of determining an enhancement parameter according to a type and a width of the enhancement parameter will be described in detail. FIG. 6 is an exemplified view showing an enhancement function graph according to an exemplary embodiment. In FIG. 6, a horizontal axis may refer to an input brightness value, a vertical axis may refer to an output brightness value, and a slope may refer to contrast generated by an enhancement function.

An enhancement function may be designed to reduce contrast in an area of disinterest (AOD) having excess-contrast in an X-ray image, and to enhance contrast in an area of interest (AOI) having subtle-contrast.

Referring to FIG. 6, in an area in which an input brightness value is subtle, specifically, below an inflection point Q (and 0 or more), an enhancement function may follow a curve in which an output brightness value sharply increases compared to an input brightness value. As a result, the enhancement function may further enhance contrast of the AOI. However, in an area over the inflection point Q, the enhancement function may converge to a preset value. As a result, contrast of the AOD, that is, not the AOI, may be reduced, and when the convergence value is set in a dynamic range, a brightness value of the AOD may be reduced in the dynamic range. According to an exemplary embodiment, the enhancement function may be realized by multiplying a first function which is designed to reduce contrast of an AOD by a second function which is designed to enhance contrast of an AOI.

For example, the first function may be designed so that an AOD having a brightness value over a dynamic range is included in the dynamic range. Specifically, in an area in which an input brightness value is close to 0, the first function may be designed so that a slope is 1 or close to 1. Since this feature results in the contrast in an MOI being 1 or close to 1, an output brightness value may have the same value as, or a similar value, to an input brightness value. However, as the input brightness value moves farther from 0, a slope of the first function, that is, contrast, may be gradually decreased. As a result, the output brightness value according to an increase of a brightness value may be converged to a preset convergence value. At this time, when the convergence value is set to a value within a dynamic range, an AOD may have contrast within the dynamic range by the first function.

In addition, the second function has a high and narrow peak in an AOI having a small input brightness value. Since a larger output brightness value compared to an input brightness value is output at a peak, the second function may enhance contrast of the AOI. However, as the input brightness value is increased in an AOD, an output brightness value converges to 1, and thus, the second function may not have an influence on contrast of the AOD.

The above-described characteristic of the enhancement function may be determined by an enhancement parameter. For example, the enhancement parameter may include an initial slope, coordinates of an inflection point, a convergence value, and a rate of convergence of the enhancement function.

The initial slope and the coordinates of the inflection point of the enhancement function may determine the enhancement characteristic of the enhancement function. For example, as an initial slope is increased and an x-coordinate of an inflection point is decreased and a y-coordinate of the inflection point is further increased, the enhancement function may enhance contrast of an output image.

Referring to FIG. 6, an enhancement function has an initial slope m and an inflection point Q (x, y). The parameter determination unit 320 may design an enhancement function in which an initial slope m and an inflection point Q (x, y) are determined according to a width of an MOI. Specifically, the parameter determination unit 320 may increase an initial slope m of an enhancement function which is applied to a detailed image having a spatial frequency corresponding to a width of an MOI, may decrease an x-coordinate, and may increase a y-coordinate. For example, as a width of an MOI is decreased, the parameter determination unit 320 may increase an initial slope m of an enhancement function applied to a detailed image of a high frequency, may increase an x-coordinate, and may increase a y-coordinate. As a result, an output brightness value at an AOI in a detailed image of the high frequency is increased and contrast of the output detailed image of the high frequency may be enhanced.

In addition, a convergence value and a rate of convergence of the enhancement function may determine a reduction characteristic of the enhancement function. For example, as a convergence value is decreased and a rate of convergence is decreased, the enhancement function may further accentuate a reduction characteristic thereof.

Referring to FIG. 6, an enhancement function may have a convergence value $k_0$, and a rate of convergence may be determined according to a value $z_1$. The value $z_1$ may refer to an input brightness value so that an output brightness value of the enhancement function has a value $k_1$ corresponding to a constant ratio of the convergence value $k_0$. Thus, as the value $z_1$ of the enhancement function may be determined, a rate of enhancement of the enhancement function may be determined. The parameter determination unit 320 may design an enhancement function in which a convergence value and a rate of convergence are determined according to a width of an MOI. Specifically, the parameter determination unit 320 may increase a convergence value $k_0$ and a rate of convergence of an enhancement function applied to a detailed image having a spatial frequency corresponding to a width of an MOI. For example, as a width of an MOI is decreased, the parameter determination unit 320 may increase a convergence value $k_0$ and a rate of convergence of an enhancement function applied to a detailed image of a high frequency. As a result, an output brightness value of a detailed image of a high frequency is increased, and a high frequency component in an enhanced image that is finally generated may be emphasized.

In addition, the parameter determination unit 320 may determine an enhancement parameter which enhances a baseband image which is a detailed image having a lowest spatial frequency among a plurality of detailed images, and may control the brightness of an enhanced image that is finally generated. As described above, since the baseband image includes information about brightness of an original image, the parameter determination unit 320 may determine an enhancement parameter applied to a baseband image so that an enhanced image that is finally generated has target brightness.

Figure 7:
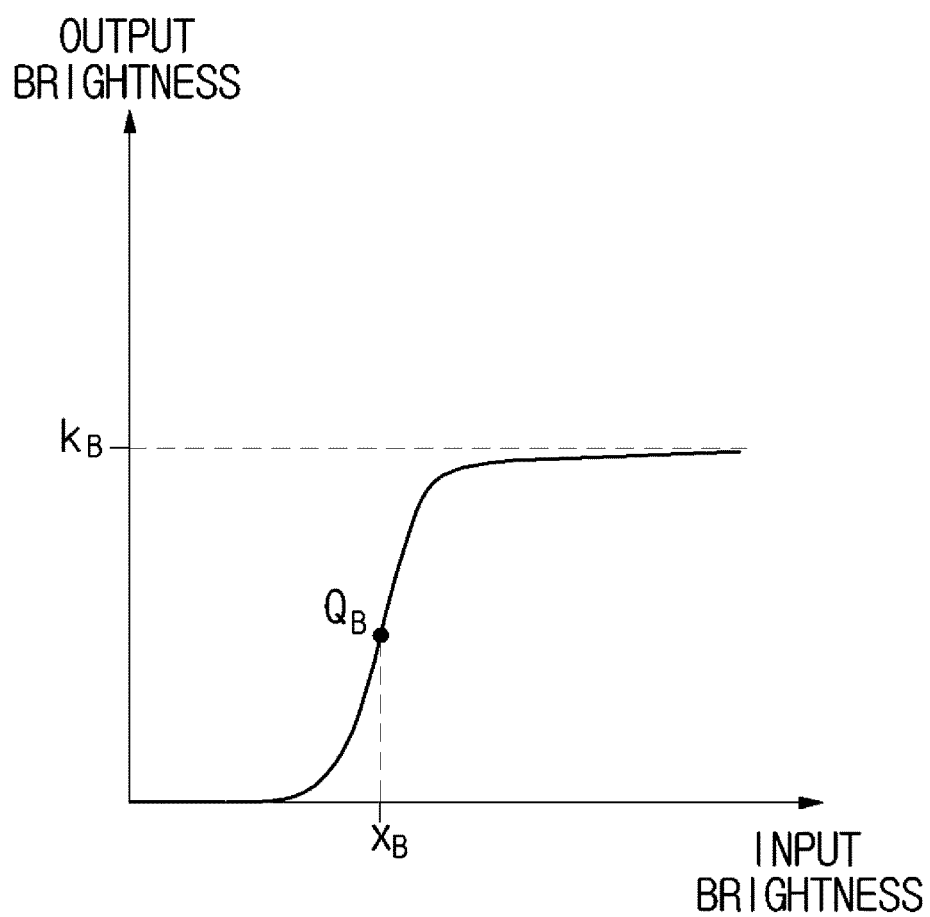
FIG. 7 is a view showing an enhancement function graph applied to a baseband image.

FIG. 7 is a view showing an enhancement function graph applied to a baseband image, and an enhancement parameter applied to a baseband image will be described with reference to FIG. 7. In FIG. 7, a horizontal axis may refer to an input brightness value, a vertical axis may refer to an output brightness value, and a slope may refer to contrast generated by an enhancement function.

As illustrated in FIG. 7, an enhancement function applied to a baseband image is separated into a diminishing area which diminishes a brightness value and an enhancing area which increases a brightness value around an inflection point $Q_B$. The diminishing area is positioned at a left side of the inflection point $Q_B$ of the baseband image and may output the output brightness of 0 or close to 0 even when an input brightness value is increased. Thus, the enhancement function applied to the baseband image may decrease and delete the brightness value included in the diminishing area. However, the enhancing area is positioned at a right side of the inflection point $Q_B$ of the baseband image, and has a constant output brightness value $k_B$. Thus, the enhancement function applied to the baseband image may output the constant brightness value $k_B$ when a brightness value included in the enhancing area is input.

Thus, as an x-coordinate of an inflection point $Q_B$ and a convergence value $k_B$ of an enhancement function applied to a baseband image are determined, the parameter determination unit 320 may enable an enhanced image that is finally generated to have a preset target brightness. Specifically, as the target brightness is increased, the parameter determination unit 320 may decrease an x-coordinate of an inflection point of an enhancement function applied to a baseband image to reduce a diminishing area and increase a convergence value. As a result, a brightness of a final output image may be increased by the enhancement function. Thus, as the parameter determination unit 320 determines an x-coordinate of an inflection point $Q_B$ and a convergence value $k_B$ of an enhancement function applied to a baseband image, the parameter determination unit 320 may be designed so that a finally generated enhancement function outputs target brightness.

As described above, as an enhancement parameter is determined based on a width of an MOI independent of contrast of an X-ray image, and thus, the X-ray apparatus may provide an enhanced image having constant contrast.

As described above, the X-ray apparatus which enhances an X-ray image and generates an enhanced image has been described. Hereinafter, an X-ray apparatus, which enhances a synthesized-image in which a plurality of X-ray images of different energy bands are synthesized and generates an enhanced image, will be described.

Figure 8:
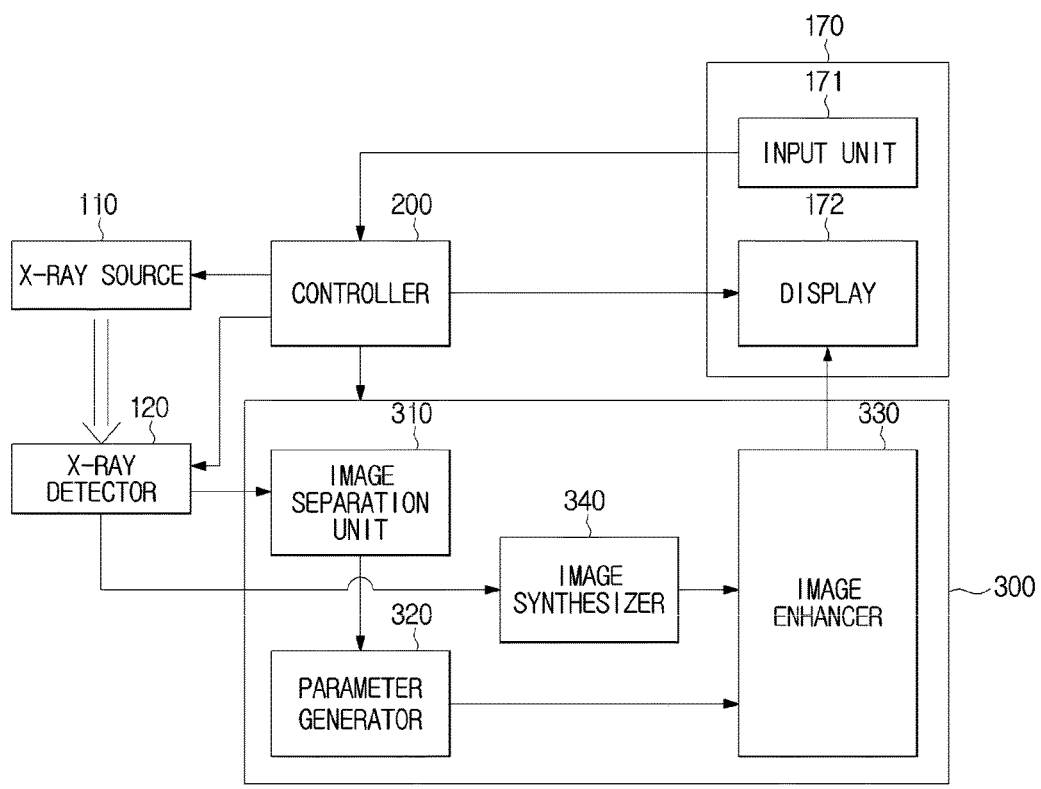
FIG. 8 is a control block diagram of an X-ray apparatus according to another exemplary embodiment.

FIG. 8 is a control block diagram of an X-ray apparatus according to another exemplary embodiment. An X-ray apparatus illustrated in FIG. 8 exemplifies a case in which an image synthesizer 340 is added to the image processor 300 in the X-ray apparatus in FIG. 2. Since the X-ray apparatus of FIG. 8 has the same configuration as that of FIG. 2 except for the image synthesizer 340, the X-ray apparatus will be described mainly based on the image synthesizer 340.

As described above, the X-ray detector 120 may generate a plurality of X-ray images of different energy bands. The plurality of generated X-ray images of the different energy bands may be synthesized into one synthesized X-ray image and may be enhanced, by the image processor 300. To this end, the image processor 300 may further include the image synthesizer 340 which synthesizes the plurality of X-ray images of the different energy bands into the one synthesized X-ray image.

The image synthesizer 340 may overlap pixels respectively corresponding to a plurality of X-ray images of different energy bands, and may synthesize one synthesized X-ray image. At this time, the image synthesizer 340 may apply a weight value to each X-ray image and may add brightness values of the pixels. Here, an applied weight value may be determined in consideration of an attenuation characteristic for an energy band. A synthesized X-ray image generated by the image synthesizer 340 may have an improved signal-to-noise ratio (SNR) compared to an X-ray image of a specific energy band generated by the X-ray detector 120. The image enhancer 330 may enhance a synthesized X-ray image which is synthesized by the image synthesizer 340, and may generate an enhanced image. The generated enhanced image may also have an improved SNR.

Figure 9:
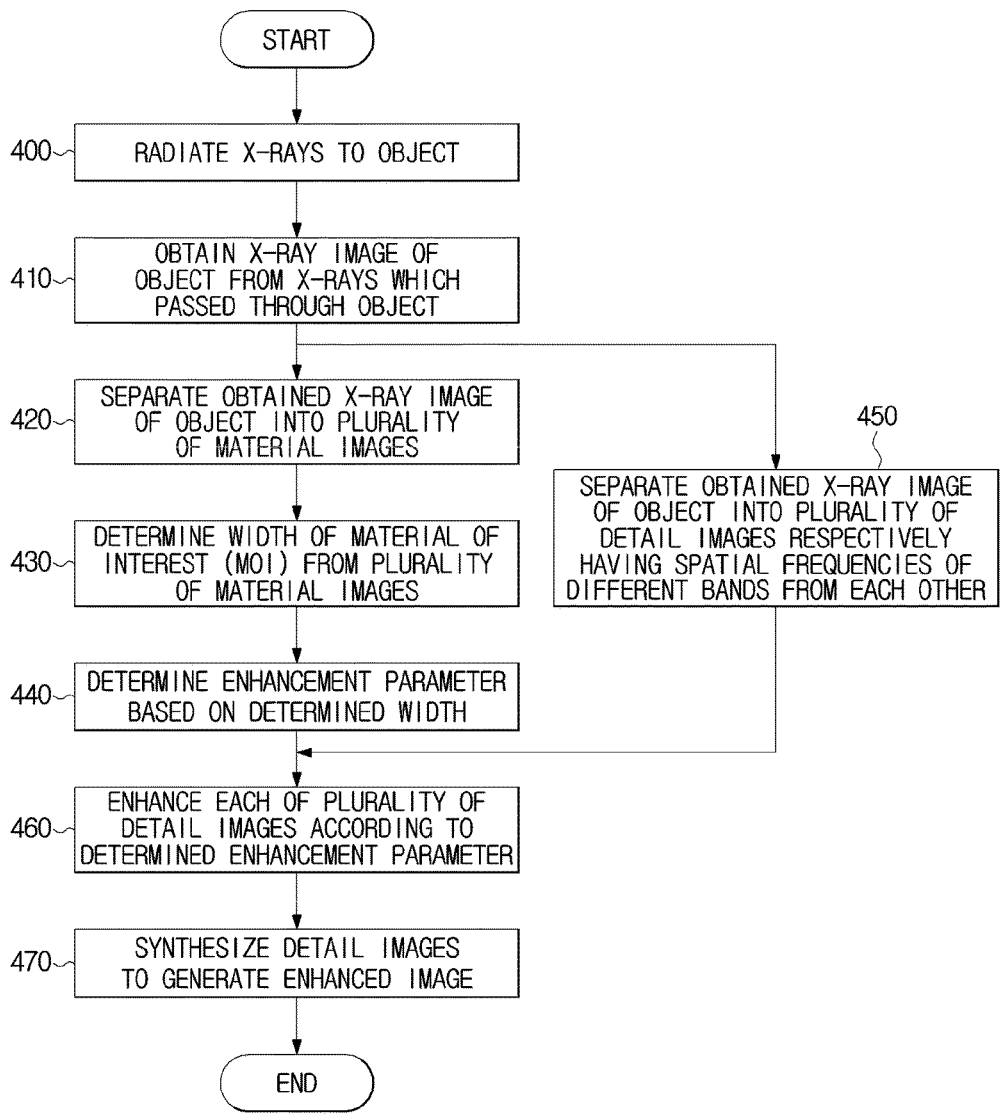
FIG. 9 is a flowchart of a control method of an X-ray apparatus according to an exemplary embodiment.

FIG. 9 is a flowchart of a control method of an X-ray apparatus according to an exemplary embodiment.

First, the X-ray source 110 may radiate X-rays to an object in operation S400. The X-ray source 110 may radiate wideband X-rays including a plurality of energy bands once, or may also radiate X-rays having different energy bands a plurality of times.

When the X-rays are radiated, the X-ray detector 120 may obtain an X-ray image of the object from the X-rays which passed through the object in operation S410. When the X-ray source 110 radiates the wideband X-rays, the X-ray detector 120 may detect and separate the X-rays for each energy band and may obtain a plurality of X-ray images of different energy bands. However, when the X-ray source 110 radiates the X-rays of the different energy bands a plurality of times, the X-ray detector 120 may detect respective radiated X-rays and may obtain each of a plurality of X-ray images of the different energy bands.

Next, a material separation unit (e.g., material separator) of the image processor 300 may separate the obtained X-ray image of the object into a plurality of material images in operation S420. According to an exemplary embodiment, the material separation unit may use the dual-energy X-ray absorptiometry in order to separate a plurality of X-ray images of different energy bands, which is the same as described above.

When the plurality of material images are separated, the parameter determination unit of the image processor 300 may determine a width of an MOI from the plurality of material images in operation S430. Here, the MOI refers to a target material to be enhanced, and the parameter determination unit may determine at least one of an average width, a maximum width, a minimum width, and a width at a preset position of the MOI as a width of the MOI.

The parameter determination unit may determine an enhancement parameter based on the determined width of the MOI in operation S440. Since the width of the MOI determined from the material image has anatomical information independent of contrast of the X-ray image generated by the X-ray detector 120, the enhancement parameter is determined based on the width. Thereby, the finally generated enhanced image may have constant contrast.

Meanwhile, the X-ray image is separated into the material images, the width of the MOI is determined, the enhancement parameter is determined based thereon, and the image enhancer 330 of the image processor 300 may simultaneously separate the X-ray image of the object into a plurality of detail images having spatial frequencies of different bands in operation S450. Here, the detailed image refers to an image forming a Laplacian pyramid, and may refer to a difference image between adjacent images among a plurality of scale images forming a Gaussian image.

When the X-ray image is separated into the plurality of detail images, the image enhancer 330 may enhance each of the plurality of detail images according to the enhancement parameter determined by the parameter determination unit in operation S460. Since each of the plurality of detailed images includes a shape or feature point corresponding to the spatial frequency, the enhancement parameters which are different from each other may be applied to each of the plurality of detail images.

Particularly, as the width of the MOI is decreased, the image enhancer 330 further enhances the detailed image of the high frequency. Thereby, a ratio of the detailed image of the high frequency may be increased in the enhanced image finally generated.

Finally, the image enhancer 330 may synthesize the enhanced detail images, and generate one enhanced image in operation S470. Since each detailed image forms a Laplacian pyramid, the image enhancer 330 may up-sample and synthesize detailed images. Thereby, the enhanced image may be easily generated.

The generated enhanced image may have constant contrast independent of contrast of the X-ray image generated by the X-ray detector 120. Thus, the enhanced image having constant contrast regardless of a subject or an imaging condition may be provided to a user.

As is apparent from the above description, an X-ray apparatus in accordance with an aspect of an exemplary embodiment determines an enhancement parameter used for enhancing an X-ray image according to a width of an MOI. Thereby, consistency of contrast of an enhanced image that is finally generated is secured.

That is, even when widths of MOIs for objects are different from each other, enhancement parameters are determined in consideration thereof, and thereby, the X-ray image can be enhanced to have constant contrast.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. An X-ray apparatus comprising:
   an image separator configured to separate an X-ray image of an object into material images representing materials in the object;
   a parameter determiner configured to determine a width of a material of interest (MOI) based on the material images, and determine an enhancement parameter configured to enhance contrast of the MOI according to the width of the MOI; and
   an image enhancer configured to separate the X-ray image into detailed images respectively including spatial frequencies of different frequency bands, enhance each of the detailed images according to the enhancement parameter, and synthesize the enhanced detailed images to generate an enhanced image.

2. The X-ray apparatus of claim 1, wherein the parameter determiner is configured to determine the enhancement parameter for each of the detailed images and further enhance a detailed image having a spatial frequency of a band corresponding to the width of the MOI, among the detailed images, based on the enhancement parameter of the detailed image having the spatial frequency of the band corresponding to the width of the MOI.

3. The X-ray apparatus of claim 1, wherein the image enhancer is configured to determine an enhancement function using the enhancement parameter, and enhance each of the detailed images according to the determined enhancement function.

4. The X-ray apparatus of claim 3, wherein the parameter determiner is configured to determine the enhancement parameter as including at least one of an initial slope, coordinates of an inflection point, a convergence value, and a rate of convergence of the enhancement function.

5. The X-ray apparatus of claim 4, wherein the parameter determiner is configured to increase the initial slope of the enhancement function applied to a detailed image of a high frequency among the detailed images, as the width of the MOI is decreased.

6. The X-ray apparatus of claim 4, wherein the parameter determiner is configured to decrease an x-coordinate of the inflection point of the enhancement function applied to a detailed image of a high frequency among the detailed images, as the width of the MOI is decreased.

7. The X-ray apparatus of claim 4, wherein the parameter determiner is configured to increase at least one of a y-coordinate of the inflection point, the convergence value, and the rate of convergence of the enhancement function applied to a detailed image of a high frequency among the detailed images, as the width of the MOI is decreased.

8. The X-ray apparatus of claim 1, wherein the parameter determiner is configured to determine the enhancement parameter of a detailed image having a preset frequency band among the detailed images so that the enhanced image has a preset target brightness.

9. The X-ray apparatus of claim 8, wherein the parameter determiner is configured to increase a convergence value of an enhancement function applied to a detailed image having the preset frequency band among the detailed images, as the preset target brightness is increased.

10. The X-ray apparatus of claim 8, wherein the parameter determiner is configured to decrease an x-coordinate of an inflection point of an enhancement function applied to a detailed image having the preset frequency band among the detailed images, as the preset target brightness is increased.

11. The X-ray apparatus of claim 1, further comprising an image synthesizer configured to synthesize X-ray images corresponding to different energy bands and provide the synthesized X-ray images to the image enhancer, wherein the X-ray image of the object includes the X-ray images corresponding to the different energy bands.

12. The X-ray apparatus of claim 1, wherein the parameter determiner is configured to determine the width of the MOI based on a number of pixels counted in a predetermined direction from an area in which the MOI is displayed in the material images.

13. A control method for an X-ray apparatus, the control method comprising:
    separating an X-ray image of an object into material images representing materials in the object;
    determining a width of a material of interest (MOI) based on the material images;
    determining an enhancement parameter for enhancing contrast of the MOI according to the width of the MOI;
    separating the X-ray image into detailed images respectively having spatial frequencies of different frequency bands;
    enhancing each of the detailed images according to the enhancement parameter; and
    synthesizing the enhanced detail images to generate an enhanced image.

14. The control method of claim 13, wherein the determining of the enhancement parameter comprises determining the enhancement parameter for each of the plurality of detailed images and further enhancing one of the detailed images having a spatial frequency of a band corresponding to the width of the MOI, among the detailed images, based on the enhancement parameter of the one detailed image.

15. The control method of claim 13, wherein the enhancing of the detailed images comprises:
    determining an enhancement function representing enhanced contrast with respect to a change in contrast of the detailed images using the enhancement parameter; and
    enhancing each of the detailed images according to the determined enhancement function.

16. The control method of claim 13, wherein the determining of the enhancement parameter comprises determining the enhancement parameter as including at least one of an initial slope, coordinates of an inflection point, a convergence value, and a rate of convergence of the enhancement function.

17. The control method of claim 16, wherein the determining of the enhancement parameter comprises increasing the initial slope of the enhancement function applied to a detailed image of a high frequency among the detailed images, as the width of the MOI is decreased.

18. The control method of claim 16, wherein the determining of the enhancement parameter comprises decreasing an x-coordinate of the inflection point of the enhancement function applied to a detailed image of a high frequency among the detailed images, as the width of the MOI is decreased.

19. The control method of claim 16, wherein the determining of the enhancement parameter comprises increasing at least one of a y-coordinate of the inflection point, a convergence value, and a rate of convergence of the enhancement function applied to a detailed image of a high frequency among the detailed images, as the width of the MOI is decreased.

20. The control method of claim 13, wherein the determining of the enhancement parameter comprises determining the enhancement parameter of a detailed image having a preset frequency band among the detailed images so that the enhanced image has a preset target brightness.

21. The control method of claim 13, further comprising synthesizing X-ray images corresponding to different energy bands into a synthesized X-ray image, wherein the X-ray image of the object has the X-ray images corresponding to the different energy bands,
    wherein the separating of the X-ray image into the detailed images comprises separating the synthesized X-ray image into the detailed images having spatial frequencies of the different frequency bands.

22. The control method of claim 13, wherein the determining of the width of the MOI comprises determining the width of the MOI based on a number of pixels counted in a predetermined direction from an area in which the MOI is displayed in the material images.

* * * * *